United States Patent
Bodenschatz et al.

(10) Patent No.: US 6,540,704 B1
(45) Date of Patent: Apr. 1, 2003

(54) ORTHOPEDIC BANDAGE

(75) Inventors: Stefan Bodenschatz, Buxtehude (DE); Arthur-Hugh Andrews, Kölln-Reisiek (DE); Anthony David Harman, Royston (GB); Peter Himmelsbach, Buxtehude (DE)

(73) Assignee: BSN Medical GmbH & Co. KG, Hamburg (DE)

( * ) Notice: Subject to any disclaimer, the term of this patent is extended or adjusted under 35 U.S.C. 154(b) by 0 days.

(21) Appl. No.: 09/720,474

(22) PCT Filed: Jun. 23, 1999

(86) PCT No.: PCT/EP99/04336

§ 371 (c)(1),
(2), (4) Date: Dec. 21, 2000

(87) PCT Pub. No.: WO00/00234

PCT Pub. Date: Jan. 6, 2000

(30) Foreign Application Priority Data

Jun. 1, 1998 (DE) .......................... 199 25 058
Jun. 26, 1998 (DE) .......................... 198 28 449

(51) Int. Cl.$^7$ ............................................. A61F 5/00
(52) U.S. Cl. ............................ 602/5; 602/54; 602/58
(58) Field of Search ............................ 602/52, 54, 58; 428/40, 261, 339, 355

(56) References Cited

U.S. PATENT DOCUMENTS

| | | | | |
|---|---|---|---|---|
| 3,970,717 | A | * 7/1976 | Muller-Albrecht | .......... 260/859 |
| 5,027,803 | A |   7/1991 | Scholtz et al. | ............. 128/89 R |
| 5,384,174 | A | * 1/1995 | Ward | ............................ 428/40 |
| 5,387,450 | A |   2/1995 | Stewart | ....................... 428/40 |
| 5,412,035 | A |   5/1995 | Schmitt et al. | ................ 525/93 |
| 5,603,948 | A | * 2/1997 | Merkle et al. | .............. 424/448 |

FOREIGN PATENT DOCUMENTS

| | | | |
|---|---|---|---|
| DE | 29 19 354 | 11/1979 | ........... A61F/13/04 |
| DE | 37 29 262 |  3/1989 | ................ C08J/5/10 |
| DE | 94 01 037 |  3/1994 | ................ C09J/7/04 |
| DE | 196 20 109 | 11/1997 | ................ C09J/7/04 |
| DE | 197 46 913 |  4/1999 | ........... D04B/21/14 |
| EP | 0 309 842 |  9/1988 | ......... C08F/257/02 |
| WO | 97/38646 | 10/1997 | |

* cited by examiner

Primary Examiner—Nicholas D. Lucchesi
Assistant Examiner—Lalita M. Hamilton
(74) Attorney, Agent, or Firm—Adams, Schwartz & Evans, P.A.

(57) ABSTRACT

Orthopedic bandage comprising a flexible backing material and an adhesive composition, characterized in that the adhesive composition has a thermoplastic behavior, is at least tacky above an activation temperature, forms at least partially crystalline structures below the activation temperature, and at a temperature below 40° C. has a shear modulus of more than 100,000 Pa.

33 Claims, 1 Drawing Sheet

ORTHOPEDIC BANDAGE

The invention relates to an orthopedic bandage for medical applications for stabilizing and immobilizing joints and limbs.

When joints or limbs are fractured, it is conventional to use a plaster dressing in order to ensure the stabilization or immobilization of the affected body part. The plaster dressing restricts the mobility so that the bone tissue can grow back together.

Furthermore, plaster dressings may also be used in the case of ruptured ligaments in joints. In this case too, the dressing is intended to prevent any loading or movement.

Plaster dressings of this kind may comprise plaster-of-Paris bandages or synthetic plaster bandages based on reactive resin. With both systems, curing takes place by wetting with water. This, in conjunction with the reinforcing materials incorporated into the bandages, achieves the strength.

These methods are known. They are, however, not without disadvantages for the user and patient. Natural plaster dressings are relatively inexpensive, yet are heavy and of only limited durability. To apply synthetic plaster bandages, gloves must be worn. Curing of the dressings takes up to 30 minutes. The synthetic plaster bandages must be packaged very rigorously since they cure on contact with atmospheric moisture.

Injuries to ligaments in joints may also be dealt with using the functional dressing technique, known as taping. The taping technique is, moreover, a treatment method for the prophylaxis of injuries, diseases and alterations on the locomotor apparatus. The purpose of taping is to specifically mimic the capsular ligament structures and so achieve selective support and stabilization. It does not, however, achieve the immobilization that is the aim of plaster dressings.

The actual tape dressing is applied in strips comprising preferably inelastic self-adhesive bands, known as straps, or in conjunction with self-adhesive bands possessing short-pull elasticity. It protects, supports and relieves vulnerable, damaged or disrupted parts of a functional unit. It permits functional loading within the pain-free sphere of movement, but prevents extreme or painful movements. Established backing materials include, in particular, nonwovens, wovens or knits which are coated with a pressure-sensitive adhesive. These dressings remain substantially flexible even when two or more layers are applied.

A bandage suitable for immobilizing a body part is described in EP 0 352 095 B. The bandage comprises a substrate whose surfaces have been impregnated with a curable liquid compound. On the surfaces there are also covers which are pervious to water. The covers comprise, preferably, a nonwoven or woven backing comprising, inter alia, a fluoro compound or a silicone.

WO 97/38646 discloses a water-crosslinked, silicone-based bandage. No heat-activatable finish is mentioned.

U.S. Pat. No. 5,412,035 describes a heat-activatable adhesive system which recrystallizes. The necessary stability and strength for orthopedic bandages are not described, nor can they be inferred from this system by the person skilled in the art.

U.S. Pat. No. 5,387,450 describes a heat-activatable and heat-deactivatable adhesive system which exhibits small temperature transitions. The required stability and strength for orthopedic bandages are likewise not disclosed and therefore not obvious for the person skilled in the art.

DE 37 29 262 A1 discloses a thermoplastic construction material comprising a backing and a polymer preparation which comprises a meltable addition polymer, a crystallizing carboxylic acid or a carboxylic acid derivative, and, if desired, crystallization modifiers. The thermoplastic construction material may be used in particular for support dressings.

EP 0 309 842 A2 [sic] discloses a composite compound in the form of films, wound bands, or sheets, which have uniformly distributed openings having a dimension of from 1 to 12 mm, leave a free passage of at least 40% of the total surface area, are shapeable at a temperature in the range from 35 to 90° C., and adhere to themselves. They are combined with a wide-mesh textile substrate having a specific weight of not more than 500 $g/m^2$ whose structure is successively impregnated or coated with at least two different materials and is then again impregnated and completely enveloped, the first material, which is located in the interior or on the surface of the substrate, being from the family of the polymers, copolymers, or amorphous or semi-crystalline alloys which have a softening temperature of not more than 80° C. beyond which they exhibit a viscoelastic to rubberlike, but not liquid, behavior. The second material, which is on the outer surface of the first material, is from the family of the polymers, copolymers or semi-crystalline alloys comprising at least 80% of structural units of the aliphatic ester type, whose melting temperature is between 35 and 80° C. and which, in the course of a certain period after melting, adhere to themselves, so that they may be laminated in two or more layers. DE 196 20 109 A1 describes a self-adhesively coated backing material with a hot-melt self-adhesive composition applied to the whole area of at least one side. The thermoplastic adhesive composition is foamed. At an application rate of at least 20 $g/m^2$, the product has an air permeability of at least 3 $cm^3/cm^2/s$.

It is an object of the invention to provide a bandage whose design, material and properties make it suitable for stabilizing and immobilizing joints and limbs.

This object is achieved by means of a bandage as specified in the main claim. The subclaims relate to advantageous developments of the bandage.

BRIEF DESCRIPTION OF THE DRAWINGS

Some of the objects of the invention have been set forth above. Other objects and advantages of the invention will appear as the description proceeds when taken in conjunction with the following drawings, in which.

Figure 1:
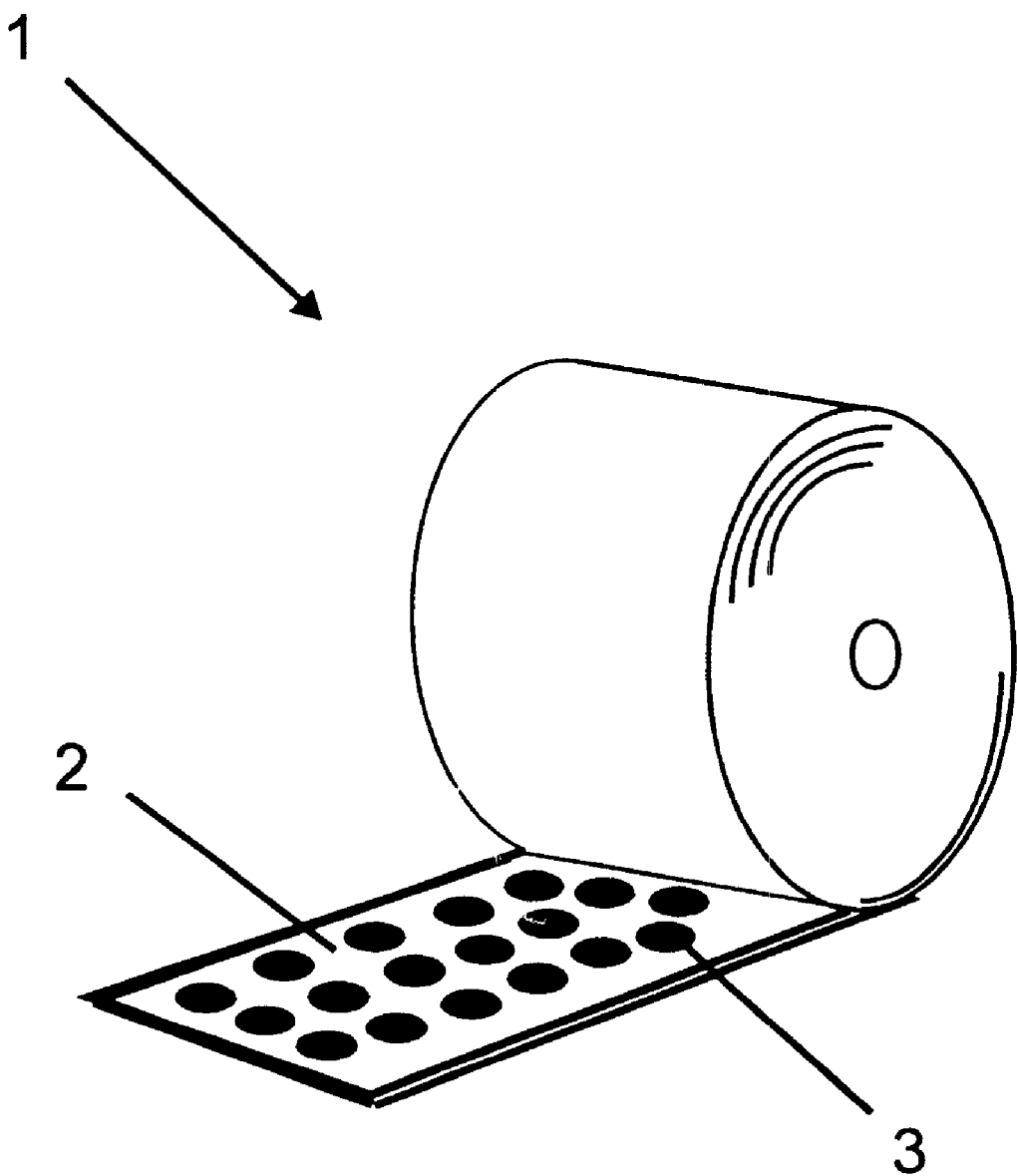
FIG. 1 is a perspective view of an orthopedic bandage according to one preferred embodiment of the invention.

The invention accordingly provides an orthopedic bandage comprising a flexible backing material and an adhesive composition, the adhesive composition
 a) having a thermoplastic behavior,
 b) being at least tacky above an activation temperature,
 c) forming at least partly crystalline structures below the activation temperature, and
 d) having a shear modulus of more than 100,000 Pa at a temperature below 40° C.

The adhesive composition may comprise thermoplastic and non-thermoplastic fractions, i.e. may overall exhibit a thermoplastic behavior. This is the case in particular when the adhesive composition consists only of thermoplastic fractions.

The activation temperature of the adhesive composition is preferably between 30° C. and 150° C.

With further preference, the orthopedic bandage is not tacky after falling below the activation temperature, i.e. in particular within a temperature range from −25° C. to 30° C.

In one preferred embodiment, the polymeric compounds in the adhesive composition are based at least in part on urethane, epoxy, urea, melamine, polyamide, polyester, polyether, saturated or unsaturated polyolefin, polyvinyl, sulfonate, acrylate or meth-acrylate compounds and/or mixtures thereof.

Polymeric compounds in the adhesive composition which comprise hydroxylpolyesterpolyurethanes or hydroxylpolyetherpolyurethanes and/or mixtures thereof are particularly preferred.

In general, the addition of tackifying resins, plastifying agents, thickeners, plasticizers, additives, fillers, pigments, fibers, stabilizers and/or active substances may lead to advantageous embodiments.

The fraction of the polymeric compound in the adhesive composition is at least 1 percent by weight. Depending on the application, the fraction of the polymeric compound may vary between 1% by weight and 100% by weight.

Finally, it has been found to be advantageous for the adhesive composition subsequently to have been chemically and/or physically crosslinked, at least in part.

The softening point of the adhesive composition is at least 40° C. Advantageous softening points for long-term applications are from 50° C. to 140° C., with particular advantage from 55° C. to 90° C.

Furthermore, the adhesive compositions of the invention exhibit an activation temperature. Above the activation temperature, the adhesive composition becomes tacky. In one specific embodiment, the activation temperature is less than the temperature at the softening point.

Depending on the formulation of the adhesive composition, its adhesion can be adjusted from very strongly self-adhesive through tacky and on to a point where it can only poorly be affixed to itself. The higher the adhesion, the better the stability of the bandage directly following application and the reliability for the therapy. Effective correction of the layers during application of the bandage may be brought about by a weak adhesive force formulation.

The adhesion depends on the nature of the polymeric compound in the adhesive composition, the molecular weight, the molecular weight distribution, the further components, and the preparation process, among other factors.

Product properties such as tack and shear stability may be quantified readily using a dynamomechanical frequency measurement. In this case, use is made of a rheometer controlled by shearing stress.

The results of this measurement method give information on the physical properties of a substance by taking into account the viscoelastic component. In this instance, at a preset temperature, of [sic] the adhesive composition is set in oscillation between two plane-parallel plates with variable frequencies and low deformation (linear viscoelastic range). Via a pickup control unit, with computer assistance, the quotient (Q=tan δ) between the loss modulus (G", viscous component) and the storage modulus (G', elastic component) is measured. A high frequency is chosen for the subjective sensing of the tack and a low frequency for the shear strength. A high numerical value denotes better tack and poorer shear stability.

$$Q = \tan \delta = G''/G'$$

| Adhesive Composition A | Temperature [° C.] | Shear stability low frequency / | Tack high frequency / |
|---|---|---|---|
| | 75 | tan δ = 2.1 | tan δ = 0.45 |
| | 25 | tan δ = 0.03 | tan δ = 0.03 |

Preference is given in accordance with the invention to heat-activatable adhesive compositions wherein the ratio of the viscous component to the elastic component at a frequency of 100 rad/s above the activation temperature is greater than 0.25.

The ratio of the viscous component to the elastic component at a frequency of 100 rad/s should at room temperature (25° C.) be less than 0.4. Moreover, at room temperature (25° C.), the ratio of the viscous component to the elastic component at a frequency of 0.1 rad/s should be less than 0.4, preferably between 0.35 and 0.02.

After falling below the activation temperature, the adhesive composition is of very low or zero adhesion. Consequently, this property enables the bandage not to stick to clothing or other articles.

Prior to the application of the bandage, it is heated to above the activation temperature of the adhesive composition and so rendered tacky. Effective strength and structural stability of the support dressing is produced by applying two or more layers of the bandage over one another.

Following the application of the bandage, the strength and structural stability increase as a result of crystalline structures which form below the activation temperature of the adhesive composition. The formation of such crystalline structures takes place within less than 2 h after cooling to a temperature below the activation temperature.

Advantageously, the formation of such crystalline structures of the adhesive composition, or of the polymeric compound used for the adhesive composition, is [lacuna] after from 10 s to 60 min, with particular preference after from 30 s to 30 min. Within this time, the bandage gains stability.

In one particular embodiment of the bandage of the invention, following application to a body part, modeling can be carried out by heating the bandage again, at least locally, above the activation temperature of the adhesive composition.

After complete stability has been reached, i.e. at a temperature of below 40° C., the shear modulus of the adhesive composition is at least 100,000 Pa, preferably from 1,000,000 Pa to 600,000,000 Pa.

The bandage is coated in particular with at least 10 g/m² adhesive composition. It is preferred to use from 40 to 1000 g/m², with particular preference from 55 g/m² to 800 g/m².

One advantageous embodiment of the adhesive composition has a density of less than 2000 kg/m³, preferably from 300 kg/m³ to 1500 kg/m³.

The adhesive composition may be used as a solution, dispersion, emulsion, or as 100% systems or combinations thereof, the choice of the appropriate coating technique being dependent on the properties of the adhesive composition. Coating techniques that may be mentioned include the customary knife, soak, pressure, spray, spin, impregnation and transfer techniques.

It is particularly advantageous if the adhesive composition at least partially penetrates or impregnates the flexible backing material, i.e. at least in certain regions sinks into the backing material and/or between the individual fibers or layers of the backing material.

It is advantageous, particularly from an environmental standpoint, to use 100% systems, since their processing does not involve a removal of the carrier matrix, i.e. of the auxiliaries, thereby increasing the processing productivity and at the same time reducing the expenditure on machinery and energy.

In one preferred embodiment, especially for use in the case of medical products, the adhesive composition is applied partially to the backing material, by means, for example, of halftone printing, thermal screen printing or gravure printing.

Preferably, the adhesive composition is applied to the backing material in the form of polygeometric domes, structures or segments.

The partial application makes it possible for the transepidermal water loss to be dissipated through regulated channels, and improves the evaporation of perspiration from the skin, especially when the backing materials used are permeable to air and water vapor. The dissipation channels employed allow the moisture to be conducted away even when a multi-ply dressing is being used.

Printed application of other shapes and patterns on the backing material is also possible—for example, a printed image in the form of alphanumeric character combinations or patterns such as lattices, stripes and zigzag lines.

In addition, the adhesive composition may also be applied, for example, by spraying, so producing a more or less irregular application pattern.

The adhesive composition may be distributed uniformly over the backing material; alternatively, it may be applied with a thickness or density which varies over the area, as appropriate for the function of the product.

Without restricting the invention, the principle of the partial application will be illustrated with reference to thermal screen printing. This consists in the use of a rotating, heated, seamless, drum-shaped, perforated, cylindrical screen which is fed via a nozzle with the thermoplastic composition. A specially shaped nozzle lip (circular or square-section coating bar) presses the thermoplastic composition, which is fed in via a channel, through the perforation of the screen wall and onto the backing web which is conveyed past it. This backing web is guided by means of a counter-pressure roller against the external jacket of the heated screen drum at a rate which corresponds to the peripheral speed of the rotating screen drum.

In this process, the resulting small domes of composition are formed in accordance with the following mechanism:

The pressure of the nozzle coating bar conveys the thermoplastic composition through the screen perforation onto the backing material. The size of the domes formed is predetermined by the diameter of the screen perforation. The screen is lifted from the backing in accordance with the rate of transportation of the backing web (rotary speed of the screen drum). As a consequence of the high adhesion of the adhesive composition and of the internal cohesion of the hot melt, the limited supply of hot-melt pressure-sensitive adhesive composition in the perforations is drawn in sharp definition from the base of the domes, which is already adhering to the backing, and is conveyed onto the backing by the pressure of the coating bar.

After the end of this transportation, the more or less highly curved surface of the dome forms over the predefined base area in dependence on the rheology of the adhesive composition. The height-to-base ratio of the dome depends on the ratio of the perforation diameter to the wall thickness of the screen drum and on the physical properties (rheology, surface tension and contact angle on the backing material) of the adhesive composition.

In one particular arrangement, at least for some of the geometric domes, structures and/or segments, the base area by means of which they adhere to the backing material is located within the projection area of the geometric domes, structures and/or segments which results from the fact that the geometric domes, structures and/or segments are projected vertically onto the backing material.

The degree of surface coverage of the coating should be at least 20%, preferably from 50% to 100%. In one particularly preferred embodiment, the degree of surface coverage should be between 75% and 95%.

It is therefore possible, by selecting particular arrangements during the manufacturing process, to achieve an air- and water-vapor-permeable coated sheetlike structure. The air permeability in this case is at least 1 cm/(cm$^2$*s). In one advantageous embodiment, it is from 15 to 70 cm/(cm$^2$*s) or more. The water vapor permeability may therefore be set at a level of greater than 500 g/(m$^2$*24 h). Special arrangements permit a water vapor permeability of greater than 1000 and 2000 g/(m$^2$*24 h).

For particular applications, it is additionally advantageous if the adhesive composition has been foamed with inert gases.

The foaming of dispersions and hot melts is part of the known prior art.

In principle, it is possible to produce foams by physical means, by chemical means, or by a combination of the two methods.

The adhesive compositions are preferably foamed using inert gases such as nitrogen, carbon dioxide, noble gases, hydrocarbons or air, or mixtures thereof. In some cases, foaming additionally by means of thermal decomposition of gas-evolving substances, such as azo, carbonate and hydrazide compounds, has been found to be suitable. The degree of foaming, i.e. the gas content, should be at least about 5% by volume and can range up to about 85% by volume. In practice, levels of from 10% by volume to 75% by volume, preferably 50% by volume, have been found appropriate. Operating at relatively high temperatures of approximately 100° C. and with a comparatively high internal pressure produces very open-pored adhesive foam layers which are particularly permeable to air and water vapor.

The use of breathable coatings in conjunction with elastic and likewise breathable backing materials produces a level of wear comfort which is perceived subjectively by the user as being pleasant.

One particularly suitable process for producing the foamed adhesive composition operates in accordance with the foam mixing system. Here, the thermoplastic adhesive composition is reacted under high pressure with the intended gases such as, for example, nitrogen, air or carbon dioxide in different volume fractions (10% by volume to 80% by volume) in a stator/rotor system and at a temperature above the softening point (approximately 120° C.).

While the gas entry pressure is greater than 100 bar, the mixing pressures between gas and thermoplastic in the system are from 40 to 100 bar, preferably from 40 to 70 bar. The adhesive foam produced in this way can be passed subsequently through a line into the applicator unit. In the applicator unit, commercially customary nozzles, extruder systems or chamber systems are used.

As a further process for the open-pored application of air- and water-vapor-permeable adhesive layers, recourse may be had to the melt-spin process or Durafiber process. The layer, applied contactlessly via a series of nozzles, arbitrarily dependent on the coating width, and spun in a weblike manner, has a much higher free surface area than do full-area coatings, and in this respect is similar to the foam application.

By virtue of the foaming of the adhesive composition and of the open pores in the composition which form as a result, and given the use of an inherently porous backing, the products coated with the adhesive composition have good permeability to water vapor and air. The amount of composition required is reduced considerably without any adverse effect on the adhesion properties. The adhesive composition possesses a surprisingly good tack, since per gram of composition there is more volume and thus more surface area for wetting of the substrate that is to be bonded, and the plasticity of the adhesive composition is increased by the foam structure; this supports the improvement in conformability. Anchoring to the backing material is also improved in this way. The foamed coating, moreover, as has already been mentioned, gives the products a soft and smooth feel.

Foaming also reduces the viscosity, in general, of the adhesive composition. This lowers the melt energy, and even thermally unstable backing materials can be coated directly.

As backing materials, descriptions have already been given of numerous materials based on films, wovens, knits, nonwovens, gels, laminates or foams, and such materials are also employed in the art.

The preferably flexible backing material may have been given a pretreatment and/or aftertreatment.

Furthermore, the bandage of the invention may be wound to a continuous roll in the form of an Archimedean spiral.

The orthopedic bandage is preferably lined with a release medium and/or provided with a wound pad or padding.

The orthopedic bandage may be sterilizable, preferably by means of γ (gamma) radiation, and the bandage may be at least partly pervious to X-rays.

In the text below, the intention is to describe the orthopedic bandage of the invention with reference to examples, without wishing to restrict the invention unnecessarily by so doing.

EXAMPLE 1

A flexible knit was soaked several times in a 50% polymer dispersion. The polymer used was a linear aliphatic thermoplastic polyurethane system which does not crosslink on exposure to water. The viscosity of the dispersion was approximately 650 mpa*s. The soak time was approximately 2 minutes per dip. The auxiliaries were evaporated between soaks. The shear modulus of the adhesive composition was $3*10^7$ (30,000,000) Pa.

The application rate of the adhesive composition was approximately 120 g/m². The treated bandage is not tacky at room temperature. The bandage was heated to 75° C. In a multi-ply application, it offered sufficient stabilization of the elbow joint. The bandage could be modeled on readily for several minutes, before recrystallization led to the desired stabilization.

EXAMPLE 2

A longitudinally elastic ideal bandage [lacuna] partially coated with a hot melt treatment. A hydroxylpolyesterpolyurethane system was used. Treatment took place at approximately 130° C. The application rate was 140 g/m². The shear modulus of the adhesive composition was $2*10^7$ (20,000,000) Pa.

For application, the bandage was heated in a convection oven to 70° C. A multi-ply dressing could be modeled on readily for several minutes. After 15 minutes, the adhesive composition attained a Shore A hardness (DIN 53505) of approximately 80. The multi-ply dressing had an air permeability of 22 cm³/(cm²*s) and a water vapor permeability of more than 1000 g/m²*24 h).

FIG. 1 shows the bandage 1 produced in accordance with Example 2, comprising a flexible backing 2 and a self-adhesive coating 3 partially applied thereon.

The bandage 1 is wound to a continuous roll in the form of an Archimedean spiral.

What is claimed is:

1. An orthopedic bandage, comprising a flexible backing material and an adhesive composition, wherein the adhesive composition has a thermoplastic behavior, is tacky at least above an activation temperature, forms at least partly crystalline structures below the activation temperature, and has a shear modulus of more than 200,000 Pa at a temperature below 40° C.

2. Orthopedic bandage according to claim 1, wherein the activation temperature of the adhesive composition is between 30° C. and 150° C.

3. Orthopedic bandage according to claim 1, wherein the activation temperature of the adhesive composition is less than the temperature at the softening point.

4. Orthopedic bandage according to claim 1, wherein after falling below the activation temperature the adhesive composition is not tacky.

5. Orthopedic bandage according to claim 1, wherein in the adhesive composition the ratio of the viscous component to the elastic component at a frequency of 100 rad/s above the activation temperature is greater than 0.25.

6. Orthopedic bandage according to claim 1, wherein the adhesive composition at a temperature of below 40° C. has a shear modulus of from 1,000,000 Pa to 600,000,000 Pa.

7. Orthopedic bandage according to claim 1, wherein the adhesive composition forms crystalline structures within from 10 s to 60 min.

8. Orthopedic bandage of claim 7 wherein said time period is 30 s to 30 min.

9. Orthopedic bandage of claim 8, wherein said time period is 2 min. to 5 min.

10. Orthopedic bandage according to claim 1, wherein the adhesive composition comprises at least in part a member of the group consisting of urethane, epoxy, urea, melamine, polyamide, polyester, polyether, saturated or unsaturated polyolefin, polyvinyl, sulfonate, acrylate or methacrylate compounds and mixtures thereof.

11. Orthopedic bandage according to claim 1, wherein the adhesive composition comprises at least one hydroxylpolyesterpolyurethane or hydroxylpolyetherpolyurethane or mixtures thereof.

12. Orthopedic bandage according to claim 1, wherein the adhesive composition is applied to the bandage with a weight per unit area of more than 10 g/m².

13. Orthopedic bandage of claim 12, wherein said weight per unit area is between 40 gm² and 1000 gm².

14. Orthopedic bandage of claim 13, wherein said weight per unit area is between 55 gm² and 800 gm².

15. Orthopedic bandage of claim 14, wherein said surface coverage is from 75% to 95%.

16. Orthopedic bandage of claim 15, wherein said air permeability is greater than 70 cm³/cm²* s.

17. Orthopedic bandage of claim 16, wherein said water vapor permeability is greater than 2000 g/m²* 24 h.

18. Orthopedic bandage according to claim 1, wherein the adhesive composition is applied to the backing material in the form of polygeometric domes, structures or segments.

19. Orthopedic bandage according to claim 1, wherein the adhesive composition is applied with a surface coverage of at least 20%.

20. Orthopedic bandage of claim 19, wherein said surface coverage is from 50% to 100%.

21. Orthopedic bandage according to claim 1, wherein the adhesive composition has been foamed with an inert gas.

22. Orthopedic bandage according to claim 1, wherein the adhesive composition at least partially penetrates or impregnates the flexible backing material.

23. Orthopedic bandage according to claim 1, wherein the orthopedic bandage is at least partly self-adhesive.

24. Orthopedic bandage according to claim 1, having an air permeability of greater than 1 $cm^3/(cm^2*s)$.

25. Orthopedic bandage of claim 24, wherein said air permeability is greater than 15 $cm^3/cm^2*$ s.

26. Orthopedic bandage according to claim 1, having a water vapor permeability of greater than 500 $g/(m^2*24\ h)$.

27. Orthopedic bandage of claim 26, wherein said water vapor permeability is greater than 1000 $g/m^2*$ 24 h.

28. Orthopedic bandage according to claim 1, which is wound to a continuous roll in the form of an Archimedean spiral.

29. Orthopedic bandage according to claim 1, lined with a release medium, provided with a wound pad or padding or a combination thereof.

30. Orthopedic bandage according to claim 1, wherein said orthopedic bandage is sterilizable.

31. Orthopedic bandage of claim 30, wherein said orthopedic bandage is sterilizable by means of γ (gamma) radiation.

32. Orthopedic bandage according to claim 1, which is at least partly pervious to X-rays.

33. Orthopedic bandage according to claim 1, wherein following application to a body part it is shapable by heating to a temperature above the activation temperature.

* * * * *